United States Patent
Wang et al.

[11] Patent Number: 6,063,095
[45] Date of Patent: *May 16, 2000

[54] METHOD AND APPARATUS FOR PERFORMING MINIMALLY INVASIVE SURGICAL PROCEDURES

[75] Inventors: Yulun Wang, Goleta; Darrin R. Uecker; Keith P. Laby, both of SB; Jeff D. Wilson, Santa Barbara; Charles S. Jordan, Santa Barbara; Modjtaba Ghodoussi, Santa Barbara; James W. Wright, Santa Barbara, all of Calif.

[73] Assignee: Computer Motion, Inc., Goleta, Calif.

[*] Notice: This patent is subject to a terminal disclaimer.

[21] Appl. No.: 09/156,994

[22] Filed: Sep. 18, 1998

Related U.S. Application Data

[63] Continuation of application No. 08/900,382, Jul. 12, 1997, abandoned, which is a continuation-in-part of application No. 08/755,063, Nov. 22, 1996, Pat. No. 5,855,583, which is a continuation-in-part of application No. 08/603,543, Feb. 20, 1996, Pat. No. 5,762,458.

[51] Int. Cl.$^7$ ...................................................... A61B 17/04
[52] U.S. Cl. .................. 606/139; 128/898; 318/568.11; 395/80; 395/86; 414/2; 901/8
[58] Field of Search .................... 606/139, 130; 128/898; 901/1, 8, 41, 48; 378/568.11; 395/80, 86; 414/1, 2

[56] References Cited

U.S. PATENT DOCUMENTS

| | | | |
|---|---|---|---|
| 4,367,998 | 1/1983 | Causer | 414/4 |
| 4,837,734 | 6/1989 | Ichikawa et al. | 364/513 |
| 4,954,952 | 9/1990 | Ubhayakar et al. | 364/513 |
| 4,980,626 | 12/1990 | Hess et al. | 318/568.16 |
| 5,357,962 | 10/1994 | Green | 128/660.07 |
| 5,382,885 | 1/1995 | Salcudean et al. | 318/568.11 |
| 5,397,323 | 3/1995 | Taylor et al. | 606/130 |
| 5,458,547 | 10/1995 | Teraoka et al. | 475/249 |
| 5,458,574 | 10/1995 | Machold et al. | 604/101 |
| 5,553,198 | 9/1996 | Wang et al. | 395/80 |
| 5,649,956 | 7/1997 | Jensen et al. | 606/205 |
| 5,735,290 | 4/1998 | Sterman et al. | 128/898 |

FOREIGN PATENT DOCUMENTS 0 776 738 A2  6/1997  European Pat. Off. .

*Primary Examiner*—Gary Jackson
*Attorney, Agent, or Firm*—Irell & Manella LLP

[57] ABSTRACT

A system for performing minimally invasive cardiac procedures. The system includes a pair of surgical instruments that are coupled to a pair of robotic arms. The instruments have end effectors that can be manipulated to hold and suture tissues. The robotic arms are coupled to a pair of master handles by a controller. The handles can be moved by the surgeon to produce a corresponding movement of the end effectors. The movement of the handles is scaled so that the end effectors have a corresponding movement that is different, typically smaller, than the movement performed by the hands of the surgeon. The scale factor is adjustable so that the surgeon can control the resolution of the end effector movement. The movement of the end effector can be controlled by an input button, so that the end effector only moves when the button is depressed by the surgeon. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft.

16 Claims, 15 Drawing Sheets

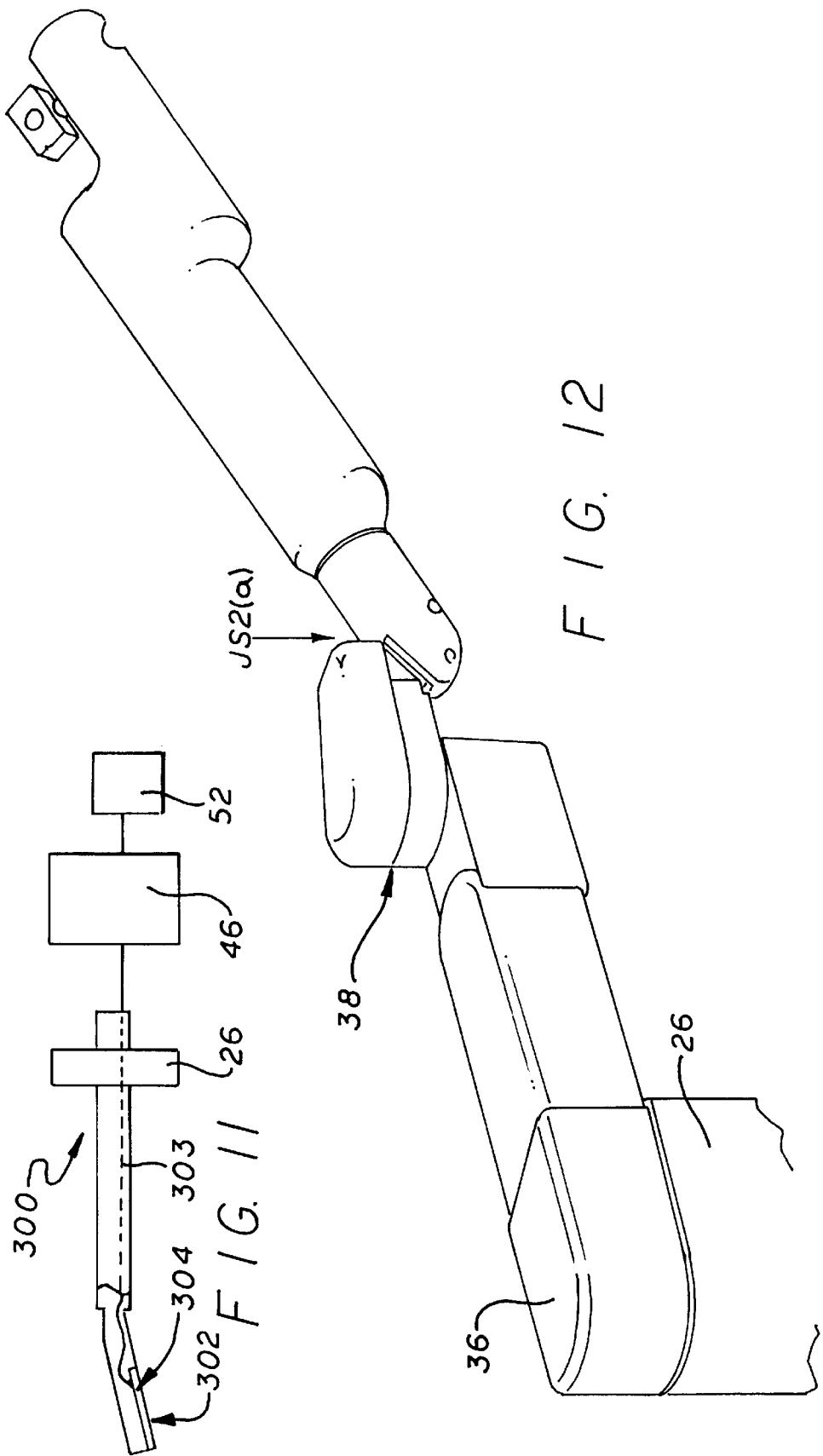

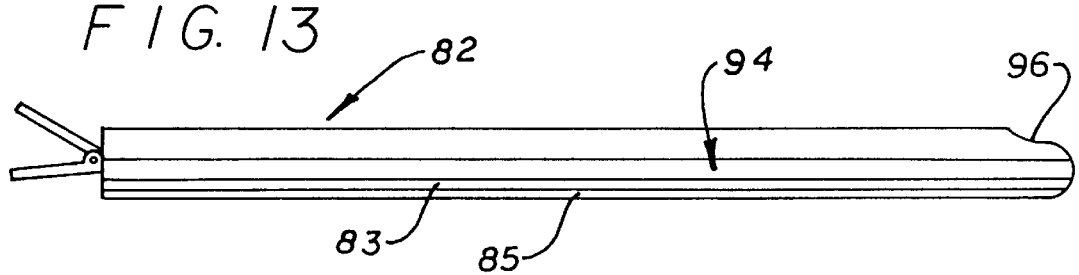
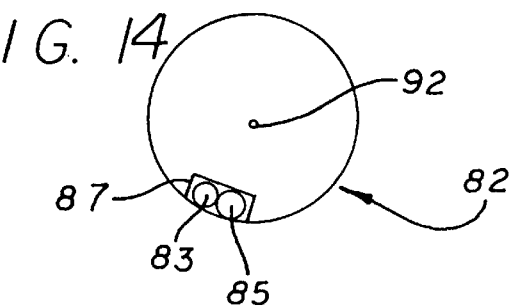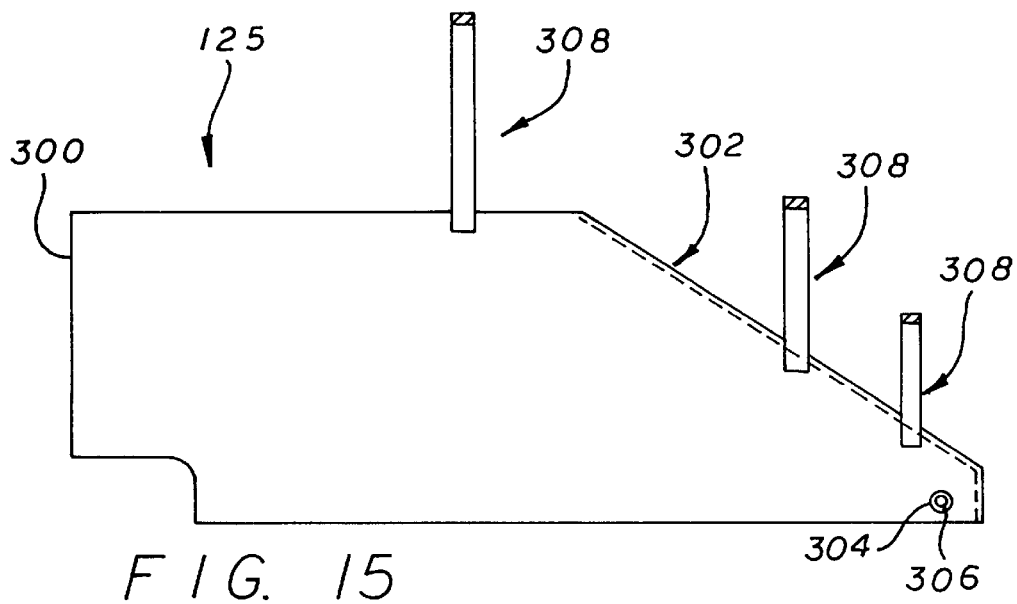

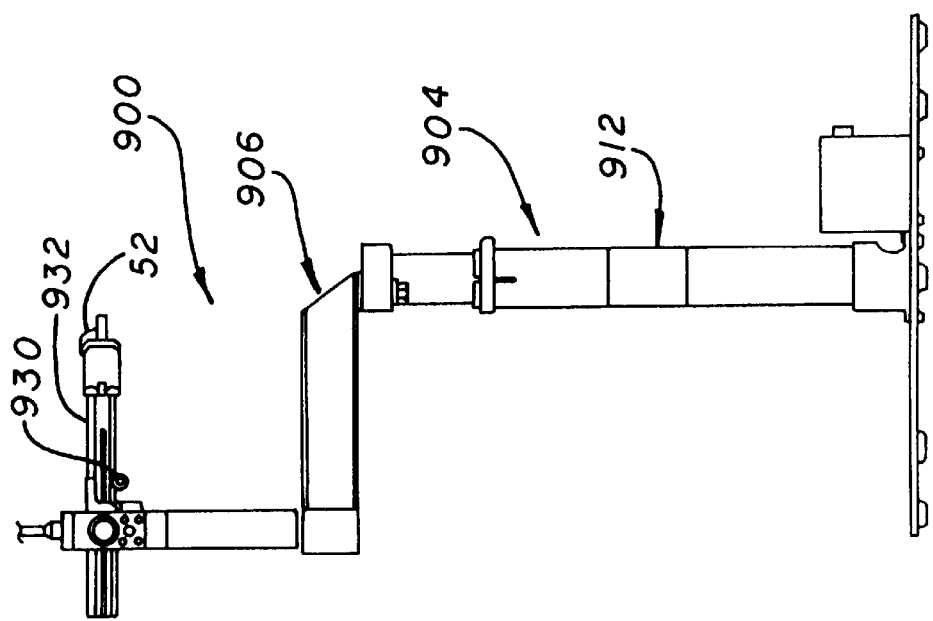
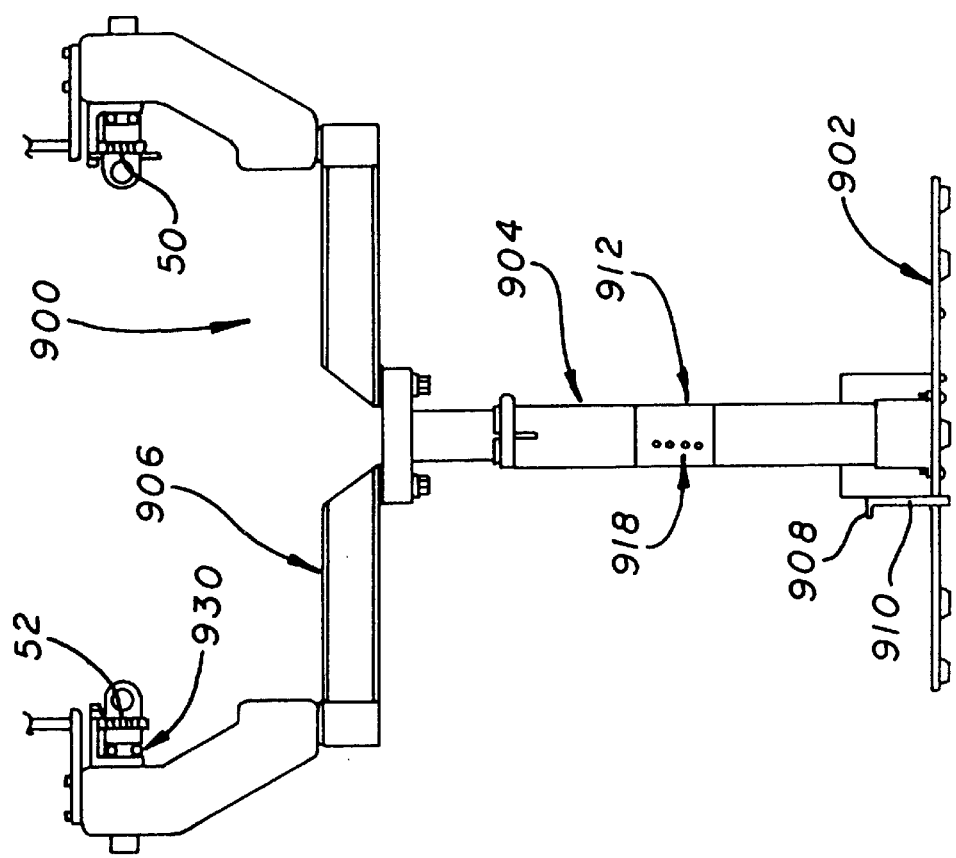

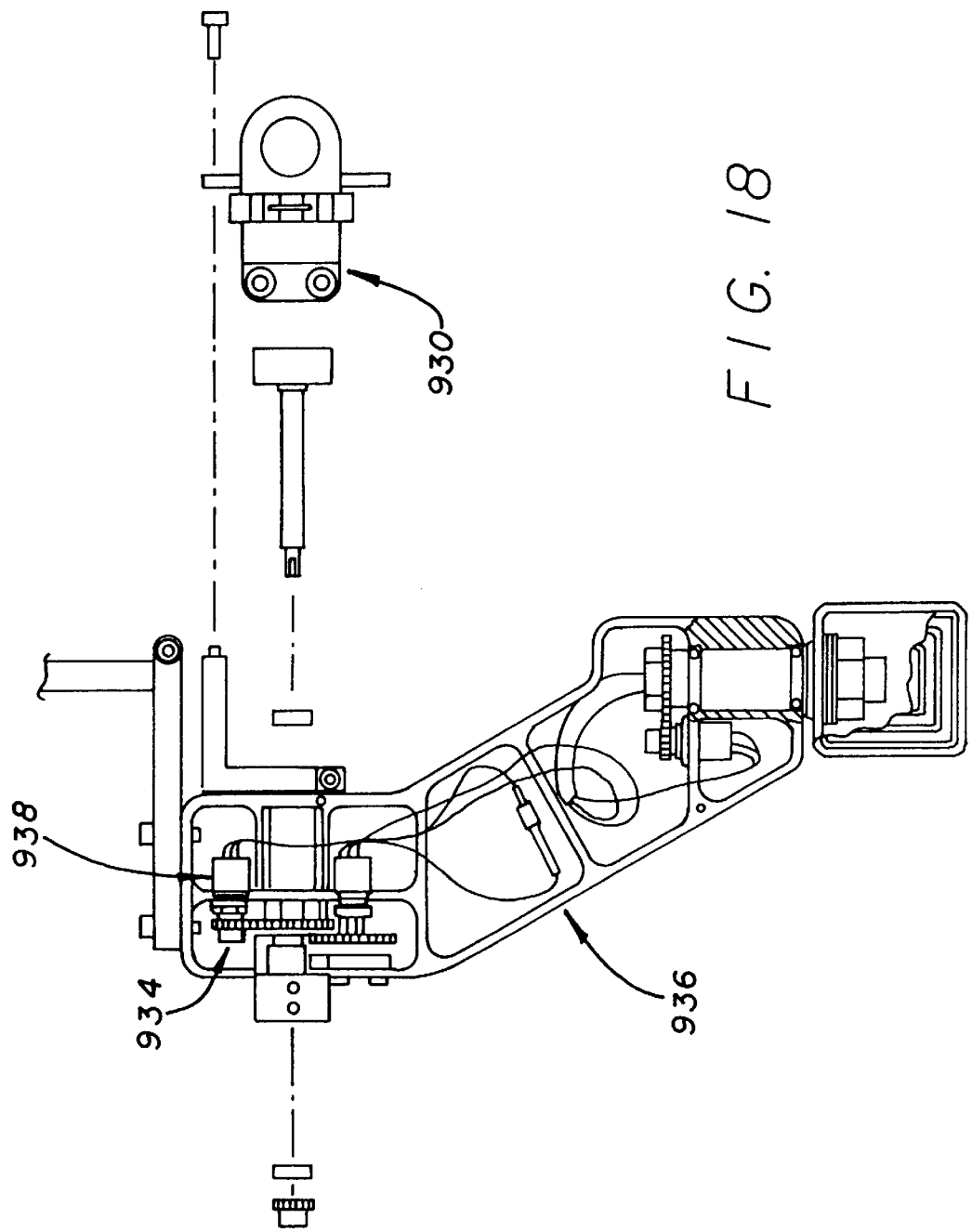

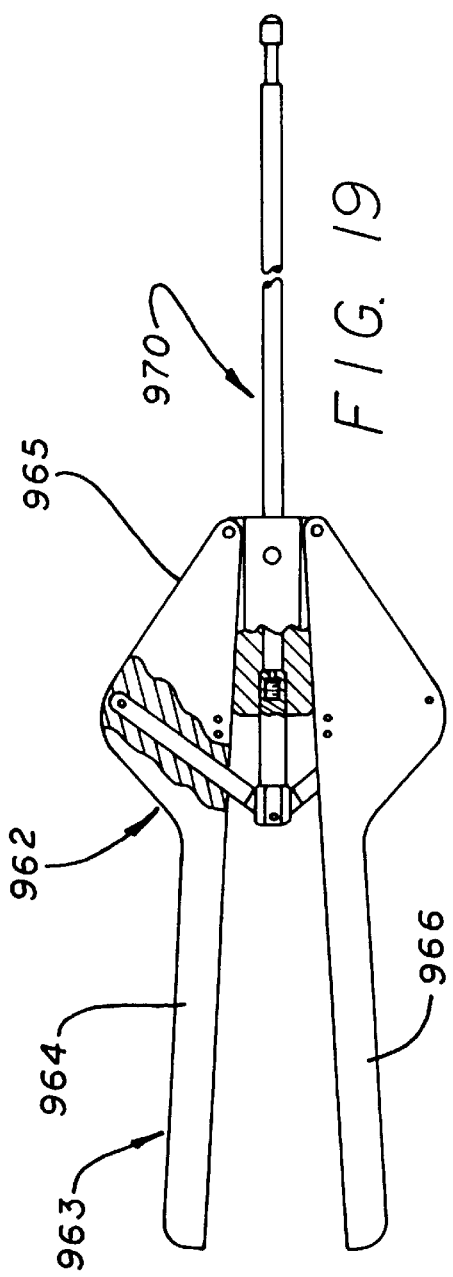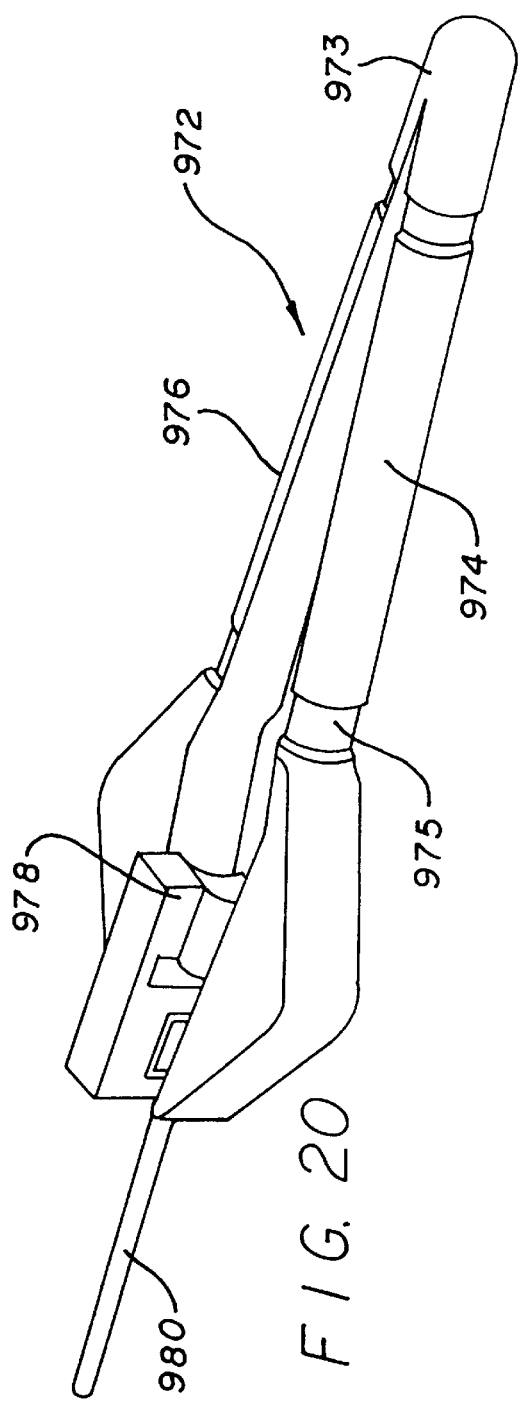

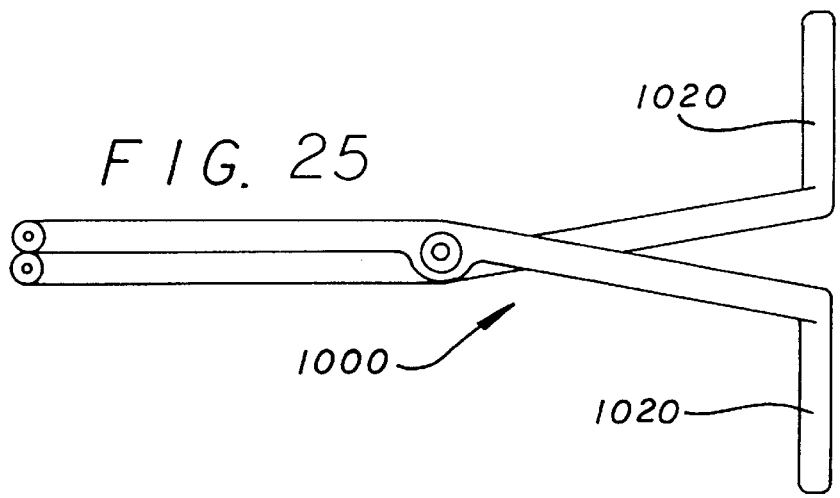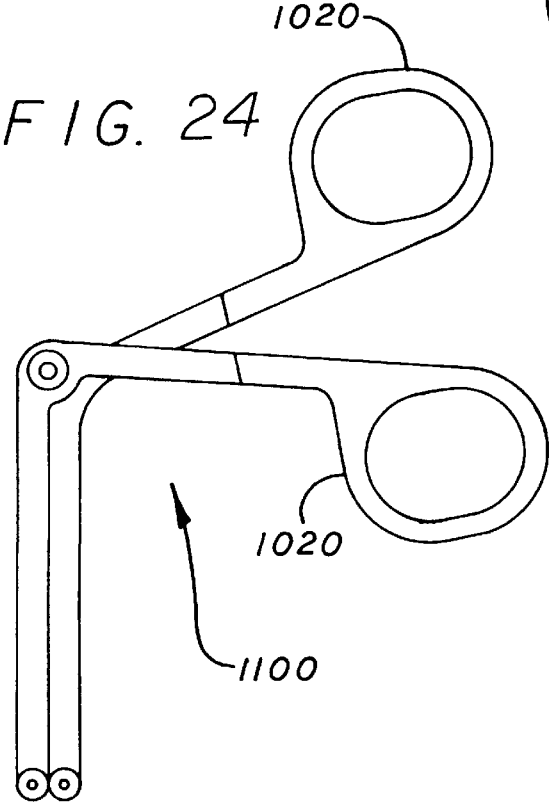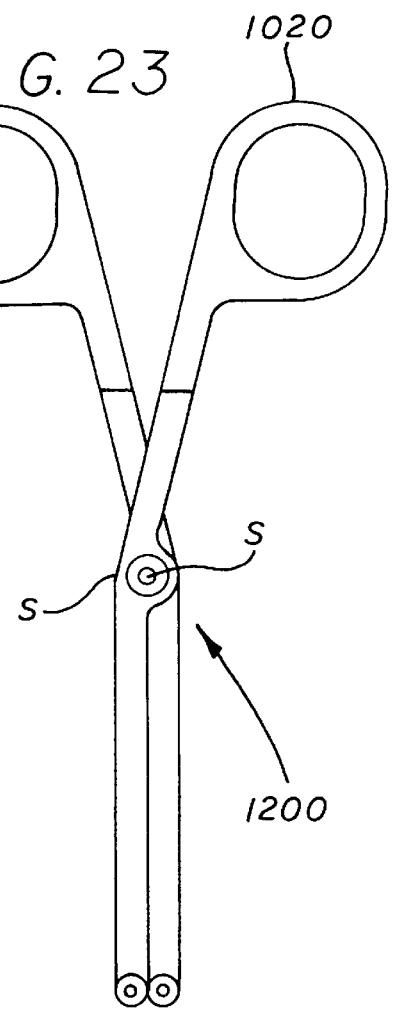

METHOD AND APPARATUS FOR PERFORMING MINIMALLY INVASIVE SURGICAL PROCEDURES

RELATION TO PREVIOUSLY FILED APPLICATIONS

The present application is a continuation of application Ser. No. 08/900,382 filed Jul. 12, 1997, now abandoned, which is a Continuation-in-part Application of U.S. patent application entitled "A Method and Apparatus For Performing Minimally Invasive Cardiac Procedures", application Ser. No. 08/755,063 filed on Nov. 22, 1996 U.S. Pat. No. 5,855,583, which is currently pending and which is a Continuation-in-part Application of U.S. Patent Application entitled "A Method and Apparatus For Performing Minimally Invasive Cardiac Procedures", which received application Ser. No. 08/603,543 was filed on Feb. 20, 1996, U.S. Pat. No. 5,762,458, and which is presently pending. Each of the three parent Applications are incorporated herein by reference.

BACKGROUND OF THE INVENTION

1. Field of the Invention

The present invention relates to a system and method for performing minimally invasive surgical procedures. More particularly, the present invention relates to a robotic system and surgical instruments that may be removably attached thereto, wherein said system aids in performing minimally invasive surgical procedures.

2. Description of Related Art

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity, commonly referred to as 'open surgery', can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and an endoscope through small incision in the skin of the patient. Manipulating such instruments can be awkward, particularly when suturing a graft to an artery. It has been found that a high level of dexterity is required to accurately control the instruments. Additionally, human hands typically have at least a minimal amount of tremor. The tremor further increases the difficulty of performing minimally invasive cardiac procedures.

To perform MIS, the surgeon uses special instruments. These instruments allow the surgeon to maneuver inside the patient. One type of instrument that is used in minimally invasive surgery is forceps, an instrument having a tip specifically configured to grasp objects, such as needles. Because forceps and other instruments designed for minimally invasive surgery are generally long and rigid, they fail to provide a surgeon the dexterity and precision necessary to effectively carry out many procedures in a minimally invasive fashion. For example, conventional MIS forceps are not well suited for manipulating a needle during a minimally invasive procedure, such as during endoscopy. Therefore, many MIS procedures that night be performed, have, as of yet, not been accomplished.

In essence, during open surgeries, the tips of the various instruments may be positioned with six degrees of freedom. However, by inserting an instrument through a small aperture, such as one made in a patient to effectuate a minimally invasive procedure, two degrees of freedom are lost. It is this loss of freedom of movement within the surgical site that has substantially limited the types of MIS procedures that are performed.

Dexterity is lacking in MIS because the instruments that are used fail to provide the additional degrees of freedom that are lost when the instrument is inserted into a patient. One problem associated with this lack of dexterity is the inability to suture when the instruments are in certain positions. As a result, surgeries that require a great deal of suturing within the surgical site are almost impossible to perform because the surgical instruments to enable much of this work are not available.

Another problem associated with MIS is the lack of precision within the surgical site. For procedures such as the MICABG (Minimally Invasive Coronary Artery Bypass Graft), extremely small sutures must be emplaced in various locations proximate the heart. As such, precise motion of the tool at the tip of a surgical instrument is necessary. Currently, with hand positioned instruments, the precision necessary for such suturing is lacking.

There are currently known several methods and systems developed to enable minimally invasive cardiac surgery. None of these systems enable completely endoscopic heart surgery (E-CABG).

As such, what is needed in the art is a method and system for performing minimally invasive microsurgery and more particularly Endoscopic CABG (E-CABG). The system should provide increased dexterity, precision and visualization within a minimally invasive surgical site.

It is to the solution of the aforementioned problems to which the present invention is directed.

SUMMARY OF THE INVENTION

The present invention is a system for performing minimally invasive surgical procedures. The system includes at least one surgical instrument coupled to at least one robotic arm. The system may include only a single surgical instrument and a single robotic arm as well as multiple instruments and multiple robotic arms as hereinbelow disclosed.

The instruments have end effectors that can be manipulated to sever, grasp, cauterize, irradiate and suture tissue and may include an irrigation and suction device. An end effector is the distal portion of the instrument the serves as the tool the surgeon desires to be using. The instruments may have articulable end effectors.

Instruments are attached at the end of an associated robotic arm. Each robotic arm may be coupled to a surgeon input device through a controller. The surgeon input device includes at least one handle. The robotic arms may be selectively connected to a specific surgeon input device handle such that a surgeon may selectively control one or more of a plurality of robotic arms, choosing which handle is connected to which robotic arm. In the preferred embodiment, there are included two handles at the surgeon input device and two associated robotic arms. However, as previously disclosed, different numbers of handles and robotic arms may be included in the system. Movement at a handle produces a corresponding movement of the end effectors and the surgical tools attached thereto. The relationship between the movement at the handles and at the instruments may be configured prior to the start of the procedure. Conversely, it may be configured during the procedure itself.

Electrical signals generated at the surgeon input device in response to movement of the handles are transmitted to the controller where the signals are processed. The controller outputs signals to the robotic arms to move the arms which accordingly move the instruments corresponding to the handle movements made at the surgeon input device. The movements at the handles of the surgeon input device may be mapped to movement at the tips of the instruments, alternatively, movement at the handles may be mapped to another point along the longitudinal axis of a corresponding instrument. As such, the surgeon can configure the system to produce different motions at the instruments in response to motions at the surgeon input device.

The movement of the handles is scaled so that the end effectors have a corresponding movement that is different, typically smaller, than the movement performed by the hands of the surgeon. It is important to appreciate that movements at the handles of the surgeon input device may be mapped to various positions along the longitudinal axis of the instrument. The scale factor is adjustable so that the surgeon can control the resolution of the end effector movement. The scale factor may be effectuated via a voice recognition system, control buttons or the like. Hand movement may be filtered, mechanically or electrically. This helps in removing any tremor the surgeon might have in their hands.

The system generally comprises:
a surgeon input device including at least one handle;
a controller connected to the surgeon input device, the controller having at least one output port for providing signals indicative of movement at the surgeon input device;
at least one robotic arm configured to receive signals from the output port of the controller; and
wherein movement of a handle at the surgeon input device results in a proportional filtered movement at the at least one robotic arm.

The system may also have one or more robotically positioned endoscopes which allow the surgeon to remotely view the surgical site. The robots that position the one or more endoscopes may be substantially similar to the robots that are included in the system that manipulate and position the surgical instruments. When using two endoscopes, an additional aperture must be made in the patient to accommodate for the second endoscope. The second endoscope may be used to provide a wide angle view of the environment.

A cardiac procedure can be performed by making small incisions or perforations through the patient's skin and inserting the instruments and endoscope(s) into the patient. The surgeon manipulates the handles and moves the end effectors to perform a cardiac procedure such as a coronary artery bypass graft or heart valve surgery. The apertures may be located at specific locations depending upon the procedure to be performed, the anatomy of the patient, or a combination of the two.

The objects and advantages of the present invention will become more readily apparent to those ordinarily skilled in the art after reviewing the following detailed description and drawings wherein:

BRIEF DESCRIPTION OF THE DRAWINGS

FIG. 8a is a side view of the master handle of the system in accordance with the present invention;

FIG. 11 is a side view of a force feedback tool in accordance with one aspect of the present invention;

FIG. 12 is a perspective view of a robotic arm including an additional joint;

FIG. 13 is a side cross sectional view of an instrument in accordance with the present invention wherein said instrument includes irrigation and suction lines;

FIG. 14 is an end sectional view of the instrument of FIG. 13;

FIG. 15 is a plan view of a drape for use with the robotic arm in accordance with the present invention;

FIG. 16 is a plan view of an alternative master-handle console in accordance the present invention;

FIG. 17 is a plan view of an alternative master-handle console in accordance with the present invention;

FIG. 18 is a partial cut away cross-section of the master handle console in accordance with the present invention;

FIG. 19 is a partial cut-away plan view of a handle in accordance with the present invention;

FIG. 20 is a perspective view of an alternative embodiment of a handle in accordance with the present invention;

FIG. 23 is an alternative embodiment of a handle in accordance with the present invention;

FIG. 24 is an alternative embodiment of a handle in accordance with the present invention; and FIG. 25 is an alternative embodiment of a handle in accordance with the present invention.

DETAILED DESCRIPTION OF THE INVENTION

Figure 1:
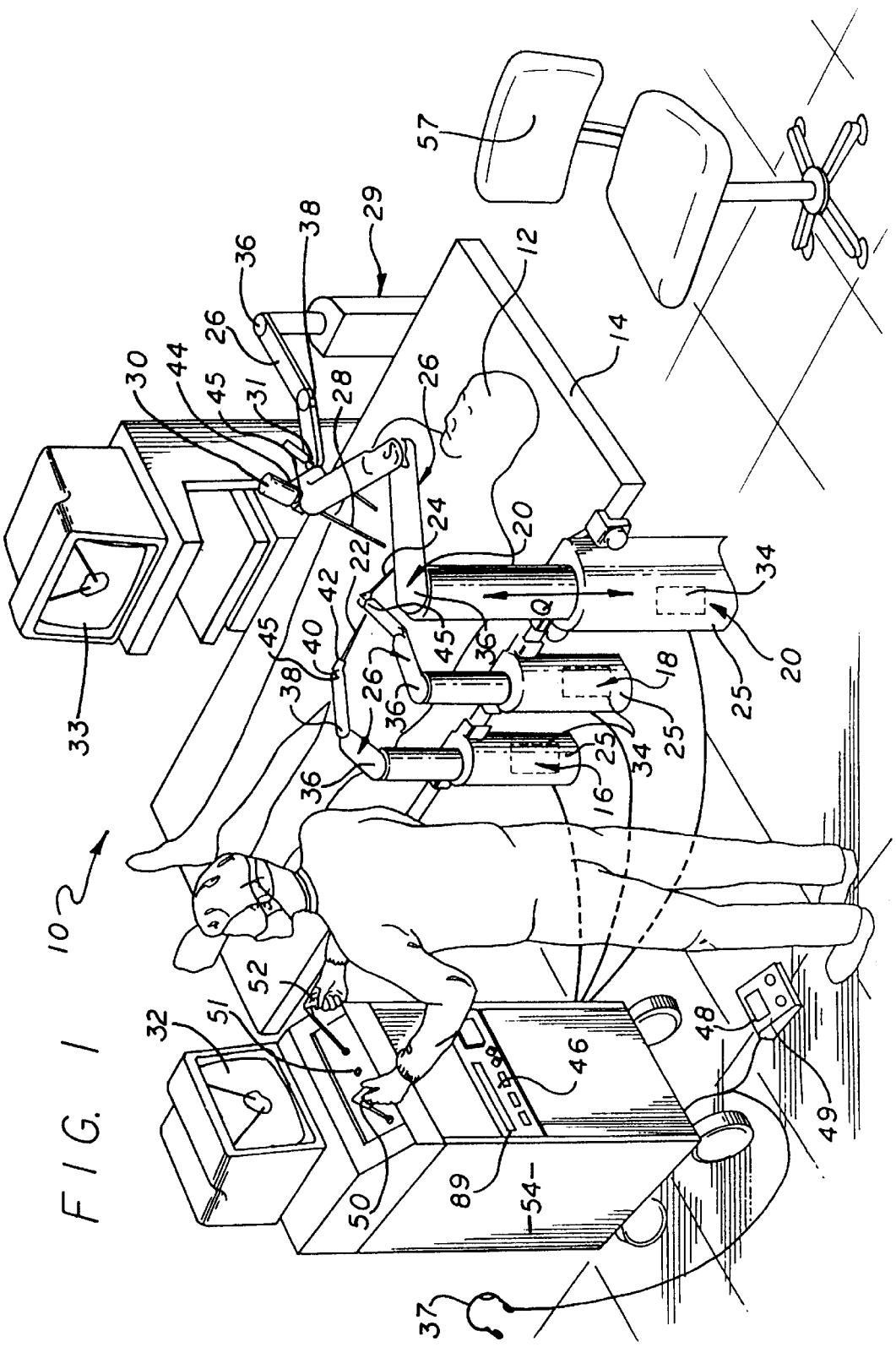
FIG. 1 is a perspective view of a minimally invasive surgical system in accordance with the present invention.

Referring to the drawings more particularly by reference numbers, FIG. 1 shows a system 10 that can be used to perform minimally invasive surgery. In a preferred embodiment, the system 10 may be used to perform a minimally invasive coronary artery bypass graft, or Endoscopic coronary artery bypass graft (E-CABG) and other anastomostic procedures. Although an E-CABG procedure is shown and described, it is to be understood that the system may be used for other surgical procedures. For example, the system can be used to suture any pair of vessels as well as cauterizing, cutting, and radiating structures within a patient. The system may additionally be used to emplace stents, or perform a transmyocardial revascularization.

The system 10 is used to perform a procedure on a patient 12 that is typically lying on an operating table 14. Mounted to the operating table 14 is, preferably, a first articulate arm 16, a second articulate arm 18 and a third articulate arm 20. The articulate arms 16–20 are preferably mounted to the table so that the arms are in a plane proximate the patient. It is to be appreciated that the arms may be mounted to a cart or some other device that places the arms proximate the plane of the patient as well. Although three articulate arms are shown and described, it is to be understood that the system may have any number of arms, such as one or more arms.

The first and second articulate arms 16, 18 and 20 each have a base housing 25 and a robotic arm assembly 26 extending from the base housing 25. Surgical instruments 22 and 24 are preferably removably coupled at the end of each robotic arm assembly 26 of the first and second articulate arms 16, 18. Each of the instruments 22, 24 may be coupled to a corresponding robotic arm assembly 26 in a variety of fashions which will be discussed in further detail hereinbelow.

The third articulate arm 20 additionally comprises a base housing 25 and a robotic arm assembly 26, and preferably has a first endoscope 28 that is attached to the robotic arm assembly 26. The base housing 25 and robotic arm assemblies 26 of each of the articulate arms 16, 18, and 20 are substantially similar. However, it is to be appreciated that the configuration of the third articulate arm 20, may be different as the purpose of the third articulate arm is to hold and position the endoscope 28 as opposed to hold and position a surgical instrument. Additionally, a fourth robotic arm 29 may be included in the system 10. The fourth arm 29 may hold a second endoscope 31 for purposes set out hereinbelow.

The instruments 22, 24 and endoscope 28 are inserted through incisions cut into and through the skin of the patient 12. The first endoscope 28 has a camera 30 that is coupled to a monitor 32 which displays images of the internal organs of the patient 12. Additionally, the second endoscope 31 may be inserted through a corresponding incision made in the patient's skin. The second endoscope 31 may be used to provide a wide field of view as depicted in FIG. 1. The second endoscope 31 is mounted to the fourth robotic arm 29 and may be coupled to a second monitor 33. As such, the surgeon is provided a close-up view of the surgical site and a wide view of the surgical site, which helps to reduce the amount of motion that must be made with the endoscopes. Essentially, the surgeon is then not required to move a single endoscope into and out of the patient, because the wide view is provided on the second monitor 33.

Each robotic arm assembly 26 has a base motor 34 which moves the arm assembly 26 in a linear fashion, relative to the base housing 25, as indicated by arrow Q. Each robotic arm assembly 26 also includes a first rotary motor 36 and a second rotary motor 38. Each of the robotic arm assemblies 26 also have a pair of passive joints 40 and 42. The passive joints 40, 42 are preferably disposed orthogonal to each other to provide pivotal movement of the instruments 22, 24 or the endoscopes 28, 31 attached to a corresponding robotic arm assembly 26. The passive joints 40, 42 may be spring biased in any specific direction, however, they are not actively motor driven. The joint angle is controlled to a particular value using a feedback control loop. The robotic arm assemblies 26 also have a coupling mechanism 45 to couple the instruments 22 and 24, or endoscope 28, 31 thereto. Each of the instruments and endoscopes has an elongated shaft:, the shaft having longitudinal axis.

Additionally, each of the robotic arm assemblies 26 has a motor driven worm gear 44 to rotate the instrument 22, 24 or endoscope 28, 31 attached thereto about its longitudinal axis. Other well-known means for spinning the instrument about its longitudinal axis may be employed as well.

The first, second, and third articulate arms 16, 18, 20 as well as the fourth arm 29 are coupled to a controller 46 which can control the movement of the arms. The arms are coupled to the controller 46 via wiring, cabling, or via a transmitter/receiver system such that control signals may be passed from the controller 46 to each of the articulate. It is preferable, to ensure error free communication between each of the articulate arms 16, 18, 20 and 29 and the controller 46 that each arm 16, 18, 20 and 29 be electrically connected to the controller, and for the purposes of example, each arm 16, 18, 20 and 29 is electrically connected to the controller 46 via electrical cabling 47. However, it is possible to control each of the arms 16, 18, 20 and 29 remotely utilizing well-known remote control systems as opposed to direct electrical connections. Such remote control systems are well-known in the art and include teleoperation via telephone lines, satellite transmissions, microwave based signals and transmitters, radio wave transmitters and receivers, or any other well-known data transmission system that exhibits high bandwidth. Because such systems are well known, they will rot be further discussed herein.

The controller 46 is connected to an input device 48 such as a foot pedal, hand controller, or voice recognition unit. For purposes of example, a foot controller and voice recognition unit are disclosed herein. The input device 48 can be operated by a surgeon to move the location of the endoscope 28 and view a different portion of the patient by depressing a corresponding button(s) disposed on the input device 48. Alternatively, the endoscope 28 may be positioned via voice control. The second endoscope may additionally be repositioned through the use of the input device 48 by switching a switch so that movements or commands made to the input device 48 control motion of the second endoscope. Using voice recognition requires essentially, a vocabulary of instructions to move the endoscope, such as "up", "down", "back", and "in" which may be recognized via a speech recognition system. The appropriate instructions are electrically sent to the controller 46. It is herein disclosed that it is preferable to use the word's "in" and "back" to effectuate movement of the endoscope into and out of the patient along the longitudinal axis thereof.

The speech recognition system may be any well-known speech recognition software. Additionally, the controller 46 includes a vocabulary of appropriate words that may be used with the system 10. Including such a vocabulary in the controller 46 may be accomplished through the inclusion of the aforementioned speech recognition software. To effectuate the voice recognition, a microphone 37 is included in the system 10. The microphone 37 may be part of a digital wireless microphone and transmitter and receiver system such that integrity of the signal is ensured. Using such a microphone system allows the surgeon to move about the operating room unencumbered by a wire that connects the microphone to an input port on the controller 46.

The controller 46 receives the input signals from the input device 48 and moves the endoscope 28 and robotic arm assembly 26 of the third articulate arm 20 in accordance with the input commands of the surgeon. Each of the robotic arm assemblies 26 may be devices that are sold by the assignee of the present invention, Computer Motion, Inc. of Goleta, Calif., under the trademark AESOP. The robotic arms and related control systems are also described in U.S. Pat. Nos. 5,515,478, and 5,524,180 which are hereby incorporated by reference.

Although a foot pedal 49 is shown and described, it is to be understood that the system may have other input means such as a hand controller, or a speech recognition interface.

The movement and positioning of instruments 22, 24 attached to the first and second articulate arms 16 and 18 is controlled by a surgeon at a pair of master handles 50 and 52. Each of the master handles 50, 52 which can be manipulated by the surgeon, has a master-slave relationship with a corresponding one of the articulate arms 16, 18 so that movement of a handle 50 or 52 produces a corresponding movement of the surgical instrument 22, 24 attached to the articulate arm 16, 18.

Additionally, a switch 51 may be included in the system 10. The switch 51 may be used by the surgeon to allow positioning of the fourth arm 29. This is accomplished because the position of the switch 51 allows the surgeon to select which of the arms a specific handle 50 or 52 controls. In this way, a pair of handles 50 and 52 may be used to control a plurality of robotic arms. The switch 51 may be connected to a multiplexer to act as a selector so that output from the multiplexer is transmitted to the appropriate robotic arm. Alternatively, the switch may have several positions and may, therefore, direct its output to the appropriate input on the controller 46.

The handles 50 and 52 may be mounted to a portable cabinet 54. A television monitor 56 may be placed onto the cabinet 54 and coupled to the endoscope 28 via well-known means so that the surgeon can readily view the internal organs of the patient 12. It is preferable that the monitor that provides the close-up view of the surgical site be proximate the surgeon so that other surgeons and nurses will not get between the surgeon and the monitor. The handles 50 and 52 are also coupled to the controller 46. The controller 46 receives input signals from the handles 50 and 52, computes a corresponding movement of the surgical instruments, and provides output signals to move the robotic arm assemblies 26 and instruments 22, 24. Because the surgeon may control the movement and orientation of the instruments 22, 24 without actually holding the ends of the instruments, the surgeon may use the system 10 of the present invention both seated or standing.

One advantage of the present system is that a surgeon may perform endoscopic surgeries in a sitting position. This helps reduce surgeon fatigue and may improve performance and outcomes in the operating room, especially during those procedures that are many hours in length. To accommodate a seated position, a chair 57 may be provided with the system.

Alternatively, and as depicted in FIGS. 16–18, the handles 50 and 52 may be mounted to a handle stand 900. The handle stand 900 essentially provides for adjustment of the height and tilt of the handles 50 and 52. The handle stand 900 includes a base 902, a neck 904 and a handle portion 906. The base 902 may be adjusted so that the handle stand 900 is tilted. A lever 908 connected to an elongated rod 910 may provide a means for tilting the handle stand 900. As such, the stand 900 may be tilted such that a surgeon using the system 10 can remain comfortable standing or sitting while manipulating the handles 50 and 52.

Additionally, the handle stand 900 may be heightened or shortened depending upon the position of the surgeon (i.e. standing or sitting). This is accomplished via a telescoping section 912. The telescoping section 912 includes an upper portion 914 telescopingly housed within a lower portion 916. A spring biased detent 918 is attached to the upper portion 914 and a plurality of apertures 920 are provided in the lower portion 916 such that the detent 918 seats in an associated aperture 920. AS such, the stand is adjustable as to height. The upper portion 914 may be extended by depressing the detent 918 and pulling up on the stand 900. Alternatively, the stand 900 may be lowered by depressing the detent and pushing down on the stand 900. The telescoping section 912 and associated mechanisms serve as a means to raise and lower the stand 900.

Additionally, and as depicted in FIGS. 16–18, the handles 50 and 52 may be attached to the stand 900 via a plurality of rollers 930 and an elongated rod 932. Motion of the rod 932 is transmitted to a plurality of gears 934 disposed on the stand 900. The gears 934 may be housed within a housing 936 to protect them from the environment and to preclude access thereto. Additionally, potentiometers 938 or some other well know means for measuring position are utilized to measure the position of the handles 50 and 52 relative to a starting position. This will be discussed in more detail hereinbelow. It is to be appreciated that the present invention may be accomplished either utilizing a cabinet 54 or a stand 900. As the handles 50 and 52 are connected to the controller 46 in either case.

Figure 2:
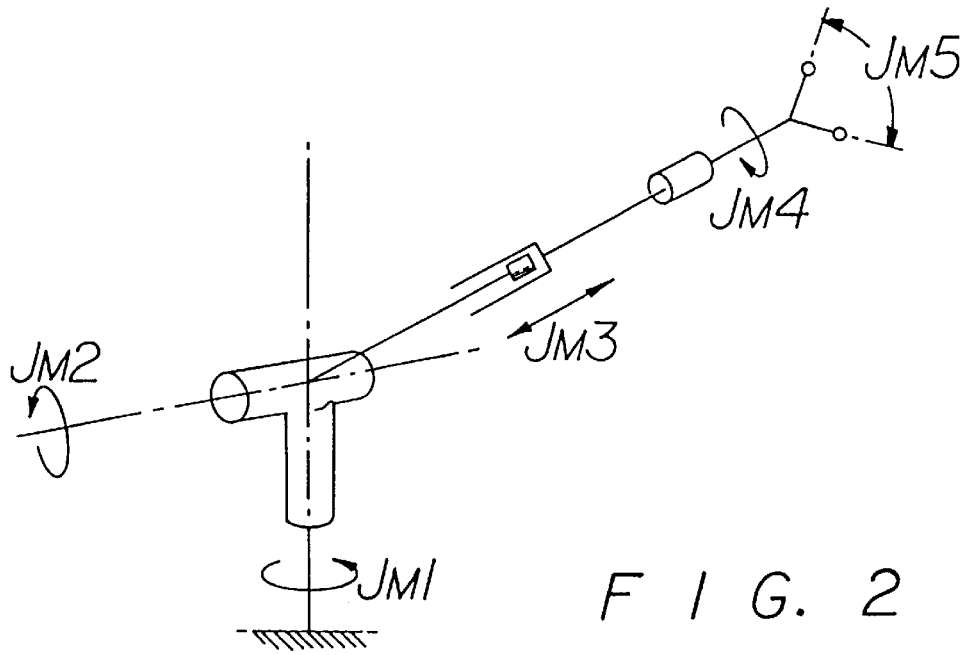
FIG. 2 is a schematic of a master of the system.

Each handle has multiple degrees of freedom provided by the various joints Jm1–Jm5 depicted in FIG. 2. Joints Jm1 and Jm2 allow the handle to rotate about a pivot point in the cabinet 54 or on the stand 900. Joint Jm3 allows the surgeon to move the handle into and out of the cabinet 54 in a linear manner or in a similar manner on the stand 900. Joint Jm4 allows the surgeon to rotate the master handle about a longitudinal axis of the handle. The joint Jm5 allows a surgeon to open and close a gripper.

Each joint Jm1–Jm5 has one or more position sensors which provides feedback signals that correspond to the relative position of the handle. The position sensors may be potentiometers, or any other feedback device such as rotary optical encoders that provides an electrical signal which corresponds to a change of position. Additionally, a plurality of position sensors may be emplaced at each joint to provide redundancy in the system which can be used to alert a surgeon of malfunctions or improper positioning of a corresponding robotic arm assembly 26.

In addition to position sensors, each joint may include tachometers, accelerometers, and force sensing load cells, each of which may provide electrical signals relating to velocity, acceleration and force being applied at a respective joint. Additionally, actuators may be included at each joint to reflect force feed back received at a robotic arm assembly 26. This may be especially helpful at joint jm5 to indicate the force encountered inside a patient by the gripper disposed at the end of one of the tools 22, or 24.

As such, a force reflective element must be included at the gripper of the instrument 22, 24 to effectuate such a force reflective feedback loop. Force reflective elements, such as a piezoelectric element in combination with a whetstone bridge are well-known in the art. However, it is not heretofore know to utilize such force reflection with such a system 10. Additionally, and as depicted in FIG. 11, a specialized tool 300 may be used in conjunction with the system 10. The tool 300 is attached to an articulate arm 26 as any other instrument used with the system. However, the instrument 300 includes force reflective elements at its tip or distal end 302. As such, the instrument may be dragged across an artery, vein or the like and provide feedback to the surgeon as to the rigidity of the vessel. A lead 303 extends the length of the instrument and connects to the controller 46 to provide electrical signals indicative of the force encountered at the instrument tip. Such signals are then processed at the controller and transmitted to the corresponding handle which provides feedback indicative of the force. Force reflection and feedback are well known in the robotics art and as such will not be further discussed herein. In this fashion, the surgeon may determine whether there is plaque built up interior the vessel proximate the area that is palpated with the device. The force sensing portion 304 is electrically connected to a corresponding handle 51, 52 through the controller 46 and the switches disclosed herein earlier.

Figure 3:
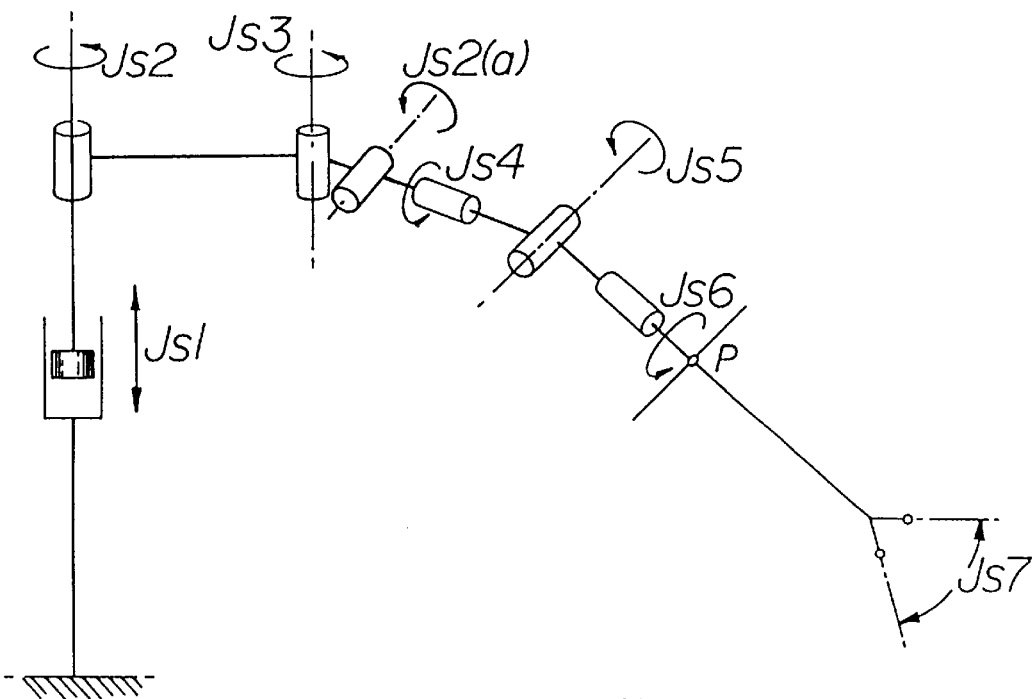
FIG. 3 is a schematic of a slave of the system.

FIG. 3 shows the various degrees of freedom of each articulate arm 16 and 18. The joints Js1, Js2 and Js3 correspond to the axes of movement of the base motor 34 and rotary motors 36, 38 of the robotic arm assemblies 26, respectively. Joint Js2(*a*) is a joint that is included directly after Joints Js2 and Js3 to provide for additional positionability of the arm 26, and more particularly an instruments disposed at the end thereof.

Joint Js2(*a*) is disposed orthogonal to both joints Js2 and Js3. Essentially, joint Js2(*a*) allows the arm 26 to be offset an angle, theta, from the plane formed by segments 36 and 38. As such, the controller must account for this offset which is measured by a potentiometer or optical encoder emplaced at the joint Js2(*a*) and is depicted in FIG. 12.

FIG. 12 shows a robotic arm including the additional joint, Js2(*a*). This joint is not motor driven, however the displacement of this joint from the plane formed by segments 36 and 38 must be accounted for to ensure proper functioning of the robotic arm. As such, and as disclosed hereinbelow, the coordinate transforms necessary to provide for movement of surgical instruments disposed at the end of the arm 26 must include transformation at this joint. Coordinate frame transforms are well know in the robotic art and as such, they will not be further discussed herein. It is the inclusion of the additional joint itself that is unobvious over the prior art. More particularly, the inclusion of the additional joint provides additional maneuverability of the robotic arm making it easier to position for use with a patient.

The joints Js4 and Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Figure 4:
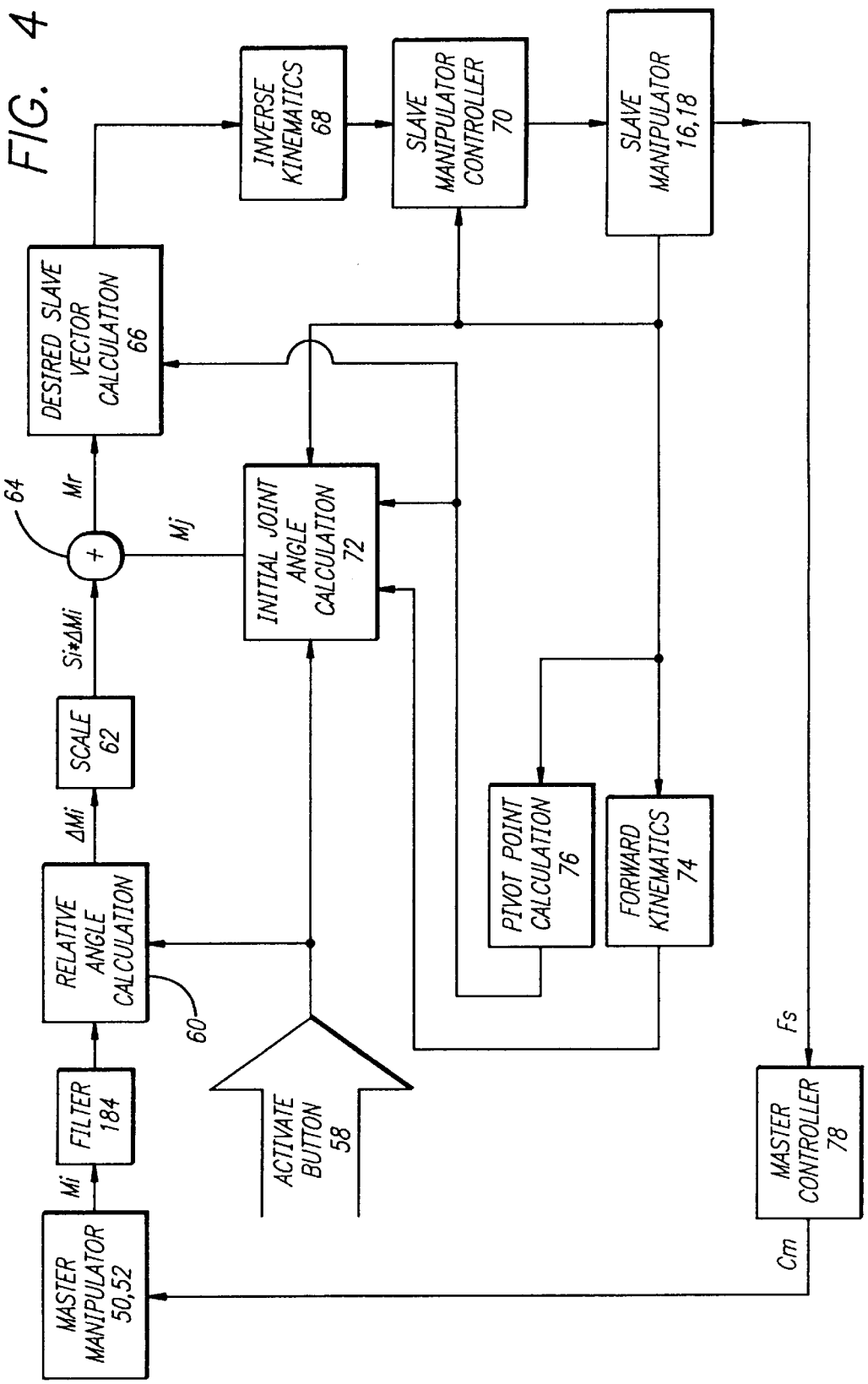
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button 58 is shown and described, it is to be understood that the surgical instrument may be activated by other means such as voice recognition. Using the voice recognition would require a specifically vocabulary such as "AWAKE" and "SLEEP" or some other two words having opposing meanings. Voice recognition is well known in general, and it is the specific use of voice recognition in this system 10 that has substantial novelty and utility.

The input button may alternatively be latched so that movement of the corresponding instrument toggles between active and inactive each time the button is depressed by the surgeon.

When the surgeon moves a handle, the position sensors provide feedback signals M1–M5 that correspond to the movement of the joints Jm1–Jm5, respectively. The controller 46 computes the difference between the new handle position and the original handle position in computation block 60 to generate incremental position values $\_M1-\_M5$.

The incremental position values $\_M1-\_M5$ are multiplied by scale factors S1–S5, respectively in block 62. The scale factors are typically set at less than one so that the movement of the instrument is less than the movement of the handle. In this manner the surgeon can produce very fine movements of the instruments with relatively coarse movements of the handles. The scale factors S1–S5 are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one are described, it is to be understood that a scale factor may be greater than one. For example, it may be desirable to spin the instrument at a greater rate than a corresponding spin of the handle.

The controller 46 adds the incremental values $\_M1-\_M5$ to the initial joint angles Mj1–Mj5 in adder element 64 to provide values Mr1–Mr5. The controller 46 then computes desired slave vector calculations in computation block 66 in accordance with the following equations.

$$Rdx = Mr3.\sin(Mr2).\cos(Mr1) + Px$$

$$Rdy = Mr3.\sin(Mr2).\sin(Mr1) + Py$$

$$Rdz = Mr3.\cos(Mr2) + Pz$$

$$Sdr = Mr4$$

Sdg=Mr5 where;

Rdx,y,z=the new desired position of the end effector of the instrument.

Sdr=the angular rotation of the instrument about the instrument longitudinal axis.

Sdg=the amount of movement of the instrument fingers.

Px,y,z=the position of the pivot point P.

The controller 46 then computes the movement of the robotic arm 26 in computational block 68 in accordance with the following equations.

$$Jsd1 = Rdz$$

$$Jsd3 = \pi - \cos^{-1}\left[\frac{Rdx^2 + Rdy^2 - L1^2 - L2^2}{2L1 \cdot L2}\right]$$

$$Jsd2 = \tan^{-1}(Rdy/Rdx) + \Delta \quad \text{for} \quad Jsd3 \leq 0$$

$$Jsd2 = \tan^{-1}(Rdy/Rdx) - \Delta \quad \text{for} \quad Jsd3 > 0$$

$$\Delta = \cos^{-1}\left[\frac{Rdx^2 + Rdy^2 + L1^2 - L2^2}{2 \cdot L1\sqrt{Rdx^2 + Rdy^2}}\right]$$

$$Jsd6 = Mr4$$

$$Jsd7 = Mr5$$

where;
Jsd1 the movement of the linear motor.
Jsd2=the movement of the first rotary motor.
Jsd3=the movement of the second rotary motor.
Jsd6=the movement of the rotational motor.
Jsd7=the movement of the gripper.
L1=the length of the linkage arm between the first rotary motor and the second rotary motor.
L2=the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases, or toggles, the input button and moves the handle. When the input button 58 is initially depressed, the controller 46 computes initial joint angles Mj1–Mj5 in computational block 72 with the following equations.

$$Mj1 = \tan^{-1}(ty/tx)$$

$$Mj2 = \tan^{-1}(d/tz)$$

$$Mj3 = D$$

$$Mj4 = Js6$$

$$Mj5 = Js7$$

$$d = \sqrt{tx^2 + ty^2}$$

$$tx = \frac{Rsx - Px}{D} \quad ty = \frac{Rsy - Py}{D} \quad tz = \frac{Rsz - Pz}{D}$$

$$D = \sqrt{(Rsx - Px)^2 + (Rsy - Py)^2 + (Rsz - Pz)^2}$$

The forward kinematic values are computed in block 74 with the following equations.

$$Rsx = L1.\cos(Js2) + L2.\cos(Js2 + Js3)$$

$$Rsy = L1.\sin(Js2) + L2.\sin(Js2 + Js3)$$

$$Rsz = J1$$

Figure 5:
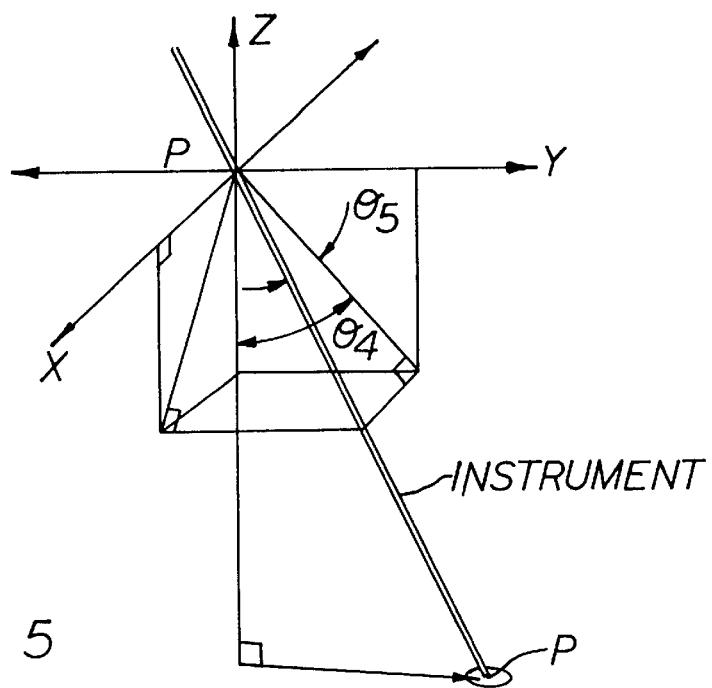
FIG. 5 is a schematic showing the instrument in a coordinate frame.

The joint angles Mj are provided to adder 64. The pivot points Px, Py and Pz are computed in computational block 76 as follows. The pivot point is calculated by initially determining the original position of the intersection of the end effector and the instrument PO, and the unit vector Uo which has the same orientation as the instrument. The position P(x, y, z) values can be derived from various position sensors of the robotic arm. Referring to FIG. 5 the instrument is within a first coordinate frame (x, y, z) which has the angles θ4 and θ5. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

Figure 6:
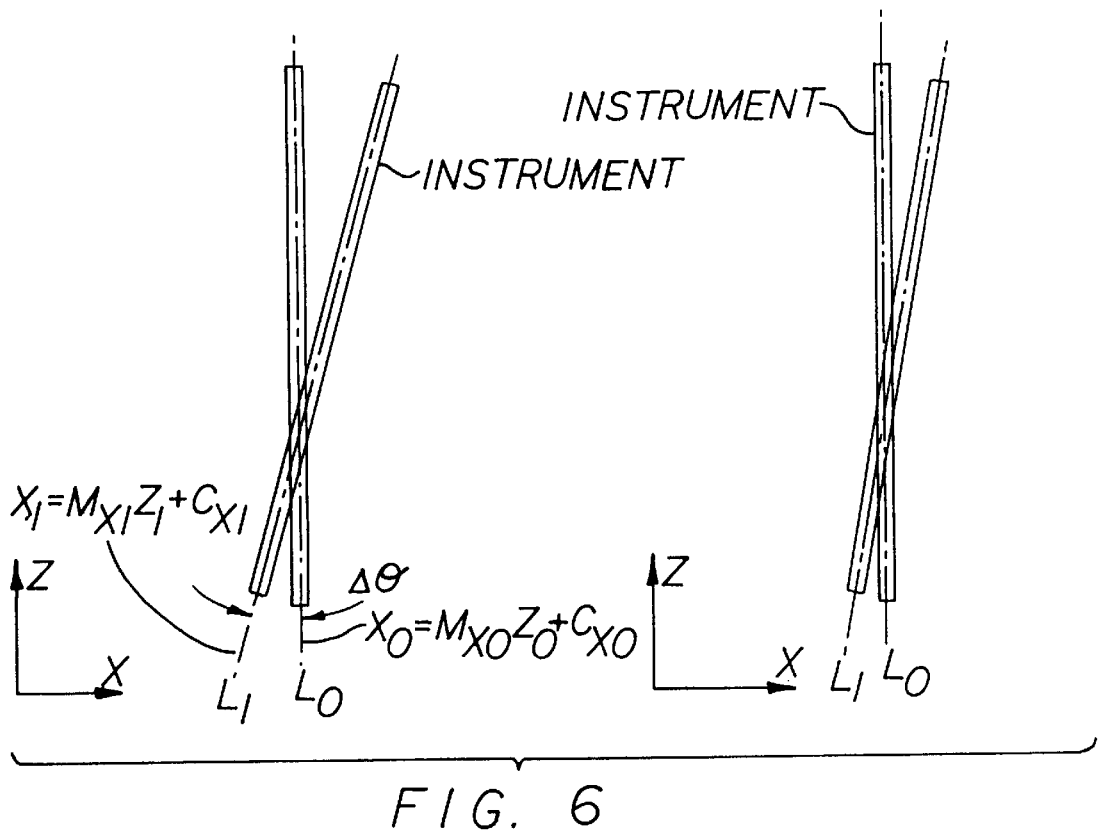
FIG. 6 is a schematic of the instrument moving about a pivot point.

After each movement of the end effector an angular movement of the instrument $\Delta\Theta$ is computed by taking the arcsin of the cross-product of the first and second unit vectors Uo and U1 of the instrument in accordance with the following line equations Lo and L1.

$$\Delta\theta = \arcsin(|\eta|)$$

$$T = Uo \times U1$$

where;
T=a vector which is a cross-product of unit vectors Uo and U1. The unit vector of the new instrument position U1 is again determined using the position sensors and the transformation matrix described above. If the angle $\Delta\theta$ is greater than a threshold value, then a new pivot point is calculated and Uo is set to U1. As shown in FIG. 6, the first and second instrument orientations can be defined by the line equations Lo and L1:

Lo:

$$xo = M_x0.Zo + Cxo$$

$$yo = M_yo.Zo + Cyo$$

L1:

$$x1 = Mx1.Z1 + Cx1$$

$$y1 = My1.Z1 + Cy1$$

where;
Zo=a Z coordinate along the line Lo relative to the z axis of the first coordinate system.
Z1=a Z coordinate along the line L1 relative to the z axis of the first coordinate system.
Mxo=a slope of the line Lo as a function of Zo.
Myo=a slope of the line Lo as a function of Zo.
Mx1=a slope of the line L1 as a function of Z1.
My1=a slope of the line L1 as a function of Z1.
Cxo=a constant which represents the intersection of the line Lo and the x axis of the first coordinate system.
Cyo=a constant which represents the intersection of the line Lo and the y axis of the first coordinate system. Cx1=a constant which represents the intersection of the L1 and the x axis of the first coordinate system.
Cy1=a constant which represents the intersection of the line L1, and the y axis of the first coordinate system.
The slopes are computed using the following algorithms:
Mxo=Uxo/Uzo
Myo=Uyo/Uzo
Mx1=Ux1/Uz1
My1=Uy1/Uz1
Cx0=Pox-Mx1.Poz
Cy0=Poy-My1.Poz Cx1=P1x-Mx1.P1z
Cy1=P1y-My1.P1z
where;
Uo(x, y and z)=the unit vectors of the instrument in the first position within the first coordinate system.
U1(x, y and z)=the unit vectors of the instrument in the second position within the first coordinate system.
Po(x, y and z)=the coordinates of the intersection of the end effector and the instrument in the first position within the first coordinate system.
P1(x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance half way between the two points Ro and R1 is computed and stored as the pivot point $R_{ave}$ of the instrument. The pivot point $R_{ave}$ is determined by using the cross-product vector T.

To find the points Ro and R1 the following equalities are set to define a line with the same orientation as the vector T that passes through both Lo and L1.

tx=Tx/Tz ty=Ty/Tz where;
tx=the slope of a line defined by vector T relative to the Z-x plane of the first coordinate system.
ty=the slope of a line defined by vector T relative to the Z-y plane of the first coordinate system.
Tx=the x component of the vector T.
Ty=the y component of the vector T.
Tz=the z component of the vector T.
Picking two points to determine the slopes Tx, Ty and Tz (eg. Tx=x1-xo, Ty=y1-yo and Tz=z1-zO) and substituting the line equations Lo and L1, provides a solution for the point coordinates for Ro (xo, yo, zo) and R1 (x1, y1, z1) as follows.

zo=((Mx1-tx)z1+Cx1-Cxo)/(Mxo-tx)

z1=((Cy1-Cyo)(Mxo-tx)-(Cx1-Cxo)(Myo-ty))/((Myo-ty)(Mx1-tx)-(My1-ty)(Mxo-tx))

yo=Myo.zo+Cyo y1=My1.z1+Cy1 xo=Mxo.zo+Cxo x1=Mx1.z1+Cx1

The average distance between the pivot points Ro and R1 is computed with the following equation and stored as the pivot point of the instrument.

$R_{ave}$=((x1+xo)/2,(y1+yo)/2,(z1+zo)/2

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

While substantial real time movement of the robotic arms is provided, it may be appreciated that pre-planned movements may be incorporated into the present system 10. This is most advantageous with regard to movement of the endoscope. Any type of movement may be stored in am associated memory of the controller so that a surgeon may define his own favorite movements and then actuate such movement by pressing a button or via voice control. Because the movement is taught in the present application as well as those patents incorporated herein by reference, no further disclosure of this concept is required.

To provide feedback to the surgeon, the system 10 may include a voice feedback unit. As such, it the robotic arms suffer any malfunction, the voice feedback may supply a message that such error has occurred. Additionally, messages regarding instrument location, time-in-use, as well as a host of other data may be supplied to the surgeon through the voice feedback unit. If such a condition occurs that requires a message, the system has a set of messages stored in an associated memory, such message may be encoded and saved in the memory. A speech synthesis unit 89, as depicted in FIG. 1 can then vocalize the message to the surgeon. In this fashion, a surgeon can maintain sight of the operative environment as opposed to looking for messages displayed on a video screen or the like. Speech synthesis is well known, although its inclusion in a master-slave robotic system for minimally invasive surgery is heretofore unknown and present novel and unobvious advantages.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

Figure 7:
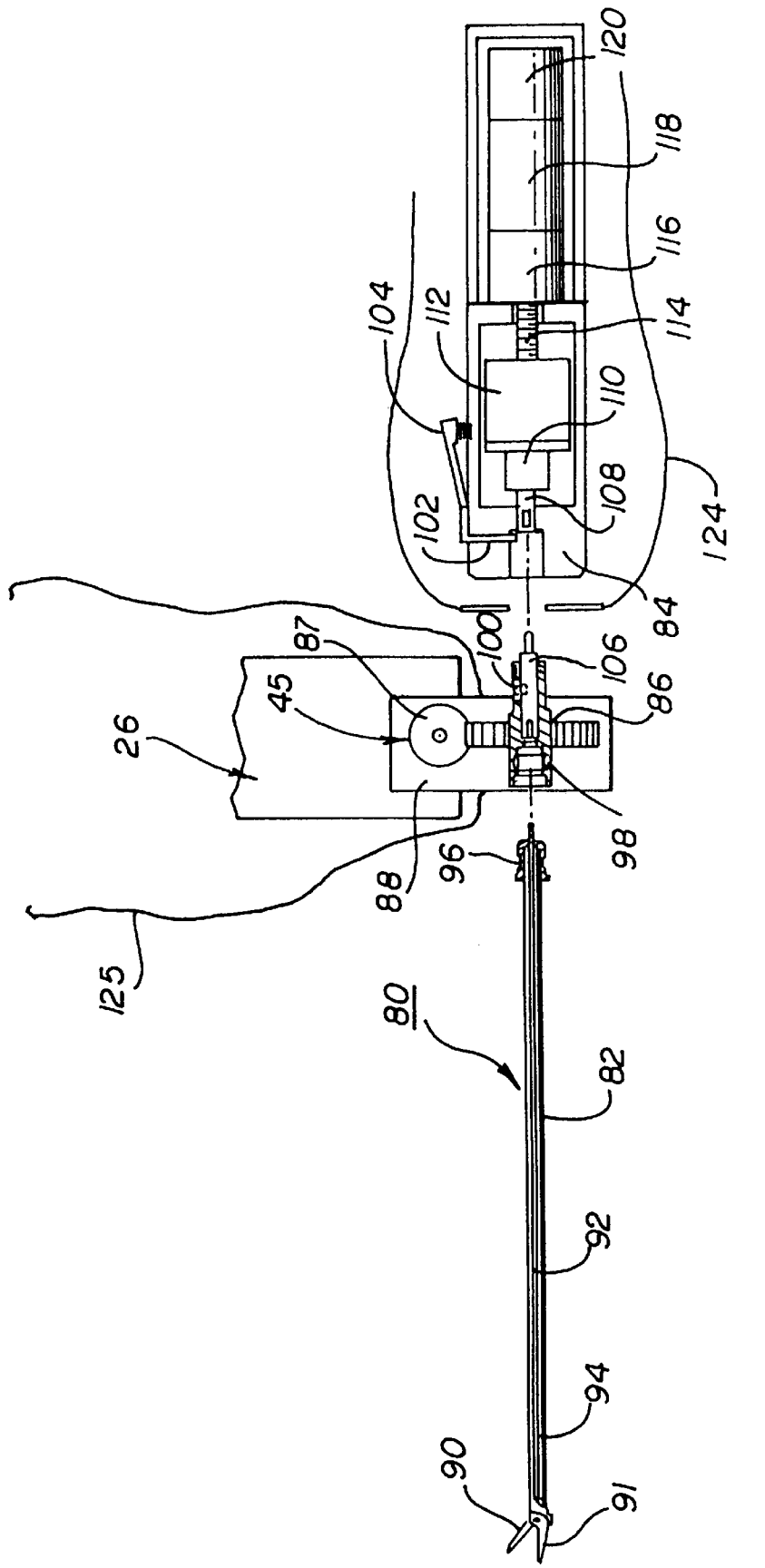
FIG. 7 is a view of an end effector in accordance with the present invention.

FIG. 7 shows a preferred embodiment of an end effector 80 that may be used in the present invention. The end effector 80 includes a surgical instrument 82, such as those disclosed hereinabove 22, 24, that is coupled to a front loading tool driver 84. The end effector 80 is mounted to one of the robotic arm assemblies 26 by coupling mechanism 45. The coupling mechanism 45 includes a collar 85 that removably attaches to a holder 86. The holder 86 includes a worm gear 87 that is driven by a motor in the robotic arm assembly 26 to rotate the collar 85 and in turn rotate the instrument 82 about its longitudinal axis. The holder 86 includes a shaft 88 that seats into a slot in the robotic arm assembly 26. The shaft 88 may be turned by the motor in the arm assembly, which then rotates the worm gear 87 thus rotating the collar 86 and the instrument 82. A tightening tool 89 may be employed to tighten and loosen the collar about the instrument 82. Such a tool operates like a chuck key, to tighten and loosen the collar 86.

The surgical instrument 82 has a first finger 90 that is pivotally connected to a second finger 91. The fingers 90, 91 can be manipulated to hold objects such as tissue or a suturing needle. The inner surface of the fingers may have a texture to increase the friction and grasping ability of the instrument 82. The first finger 90 is coupled to a rod 92 that extends through a center channel 94 of the instrument 82. The instrument 82 may have an outer sleeve 96 which cooperates with a spring biased ball quick disconnect fastener 98. The quick disconnect 98 allows instruments other than the finger grasper to be coupled to front loading tool driver 84. For example, the instrument 82 may be decoupled from the quick disconnect 98 and replaced by a cutting tool, a suturing tool, a stapling tool adapted for use in this system, such as the stapling apparatus disclosed in U.S. Pat. Nos. 5,499,990 or 5,389,103 assigned to Karlsruhe, a cutting blade, or other surgical tools used in minimally invasive surgery. The quick disconnect 98 allows the surgical instruments to be interchanged without having to re-sterilize the front loading tool driver 84 each time an instrument is plugged into the tool driver 84. The operation of the front loading tool driver 84 shall be discussed in further detail hereinbelow.

The quick disconnect 98 has a slot 100 that receives a pin 102 of the front loading tool driver 84. The pin 102 locks the quick disconnect 98 to the front loading tool driver 100. The pin 102 can be released by depressing a spring biased lever 104. The quick disconnect 98 has a piston 106 that is attached to the tool rod 92 and in abutment with an output piston 108 of a load cell 110 located within the front loading tool driver 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire end effector 80 is rotated by the motor driven worm gear 87.

In operation, the motor 118 of the front loading tool driver 84 receives input commands from the controller 46 via electrical wiring, or a transmitter/receiver system and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46.

The tool 82 and any tool included in the system may include an irrigation line 83 and a suction line 85. Each of the irrigation line 83 and suction line 85 extend down the center channel 94 and may be enclosed within a separate housing 89 disposed interior the tool 82. This is depicted in FIGS. 13 and 14. The irrigation line 83 is connected to a water source or saline source and may be used to irrigate the surgical site or to remove tissue from the instrument 82. Irrigation systems are generally well known. It is not heretofore known, though, to include an irrigation line 83 into an endoscopic instrument for use with a robotic system 10.

Additionally, a suction line 85 may be enclosed within the housing 89 disposed interior the instrument 82. Suction is generally needed to remove blood, or other fluids from the surgical site. Again, it is not heretofore known to include a suction line 85 in an endoscopic instrument for use with a robotic system 10. As such, the inclusion of either an irrigation line or a suction line present advances in the art that are novel and as of yet unknown.

Each of the suction and irrigation lines run to well-known suction and irrigation systems which are well known in the art. The activation of irrigation or suction is generally accomplished through the use of a foot controller or hand controller. However, it must be appreciated that the activation of such devices may be integrated into the present system by including a button at the surgeon input device or the cabinet. Alternatively, the suction and irrigation may be voice activated and as such, additional vocabulary must be included in the voice recognition system of the present invention. More particularly, the voice recognition system should recognize the commands "suction" and "irrigate".

The front loading tool driver 84 may be covered with a sterile drape 124 so that the tool driver 84 does not have to be sterilized after each surgical procedure. Additionally, the robotic arm assembly 26 is preferably covered with a sterile drape 125 so that it does not have to be sterilized either. The drapes 124, 125 serve substantially as a means for enclosing the front loading tool driver 84 and robotic arm assembly 26. The drape 125 used to enclose the robotic arm assembly 26 is depicted in further detail in FIG. 26. The drape 125 has a substantially open end 300 wherein the robotic arm assembly 26 may be emplaced into the drape 125. The drape 125 additionally includes a substantially tapered enclosed end 302 that effectively separates the arm assembly 26 from the operating room environment. A washer 304 having a small aperture 306 formed therethrough allows an instrument to be coupled to the arm assembly 26 via the coupling mechanism 45. The washer 304 reinforces the drape 125 to ensure that the drape 125 does not tear as the arm assembly 26 moves about. Essentially, the instrument cannot be enclosed in the drape 125 because it is to be inserted into the patient 12. The drape 125 also includes a plurality of tape 308 having adhesive 310 disposed thereon. At least one piece of tape 308 is opposedly arranged the other pieces of tape 308 to effectuate the closing of the drape 125 about the arm assembly 26.

Figure 8:
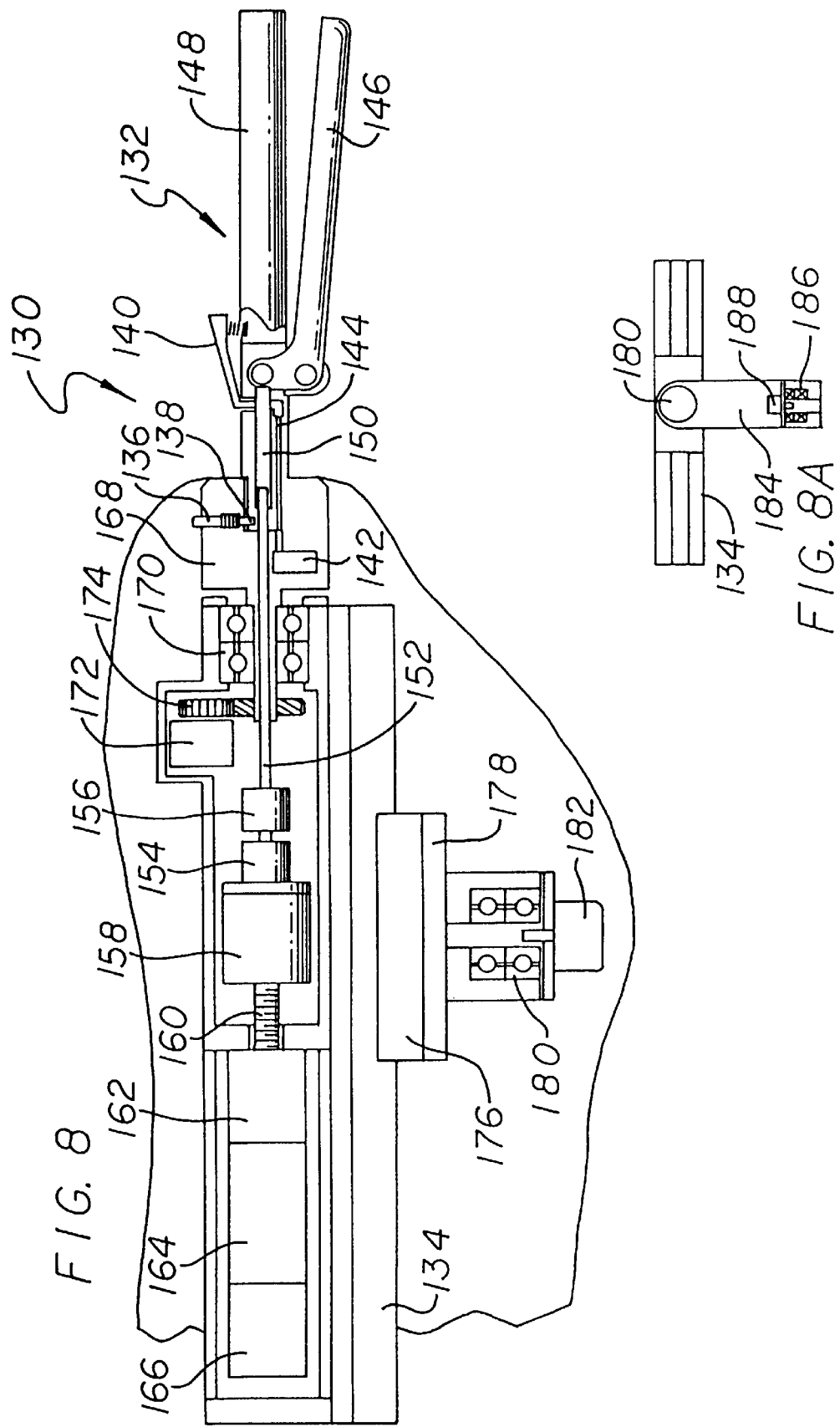
FIG. 8 is a view of a master handle of the system in accordance with the present invention.
Figure 9:
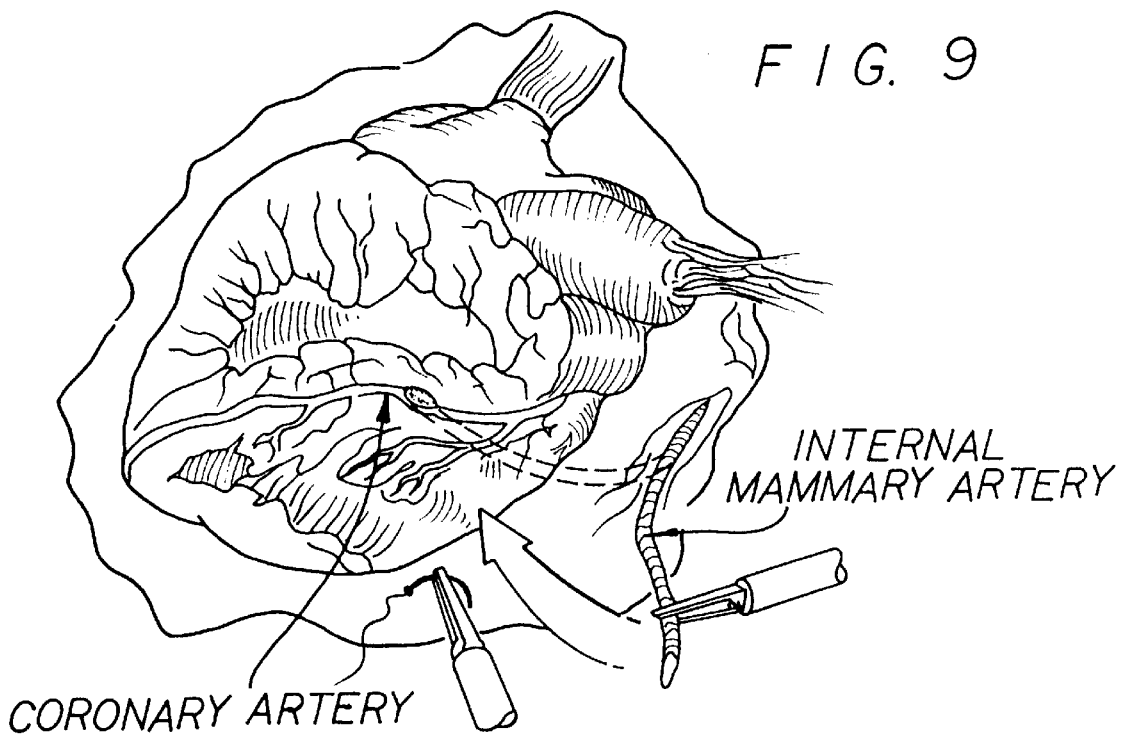
FIGS. 9–10A–I are illustrations showing an internal mammary artery being grafted to a coronary artery.

FIGS. 8 and 8a show a preferred embodiment of a master handle assembly 130. The master handle assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector. As disclosed hereinabove, an instrument may be provided that is used to just sense the rigidity of a vessel. This instrument includes a single plate and is depicted in FIG. 11.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. Additionally, an optical encoder may be employed for this purpose. Alternatively, both a potentiometer and an optical encoder may be used to provide redundancy in the system. The swivel movement is translated to a corresponding spin of the end effector by the controller and robotic arm assembly. This same type of assembly is employed in the stand 900.

The arm 134 may be coupled to a linear bearing 176 and corresponding position sensor 178 which allow and sense linear movement of the handle. The linear movement of the handle is translated into a corresponding linear movement of the end effector by the controller and robotic arm assembly. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm assembly.

A human hand will have a natural tremor typically resonating between 6–12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6–12 hertz. Alternatively, an optical encoder and digital filter may be used for this purpose.

As shown in FIGS. 9 and 10A–I, the system is preferably used to perform a cardiac procedure such as a coronary artery bypass graft (CABG). The procedure is performed by initially cutting three incisions in the patient: and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery.

Figure 10A:
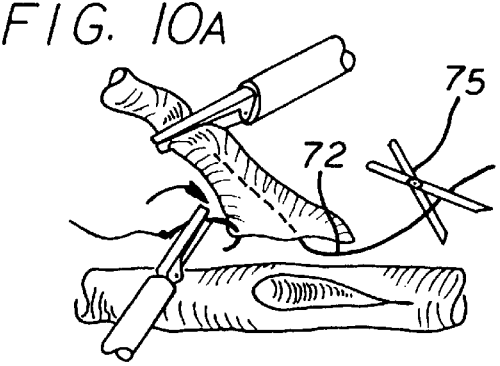
Figure 10B:
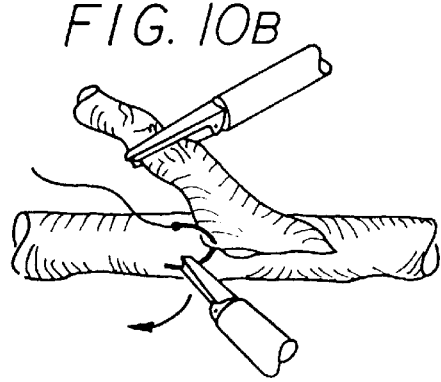
Figure 10C:
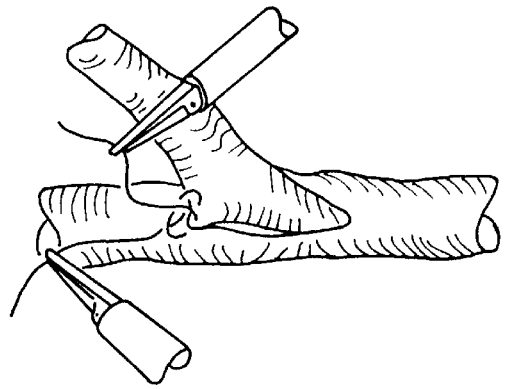
Figure 10D:
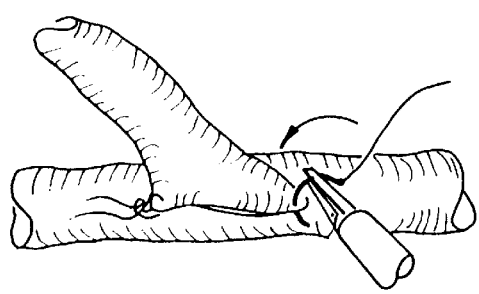
Figure 10E:
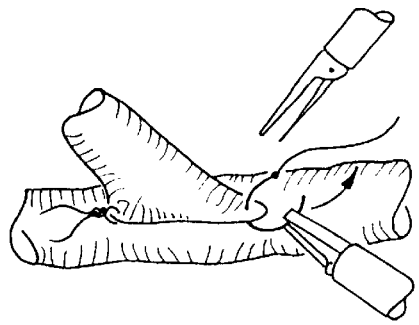
Figure 10F:
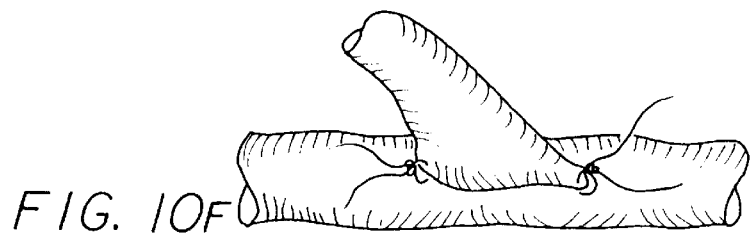
Figure 10G:
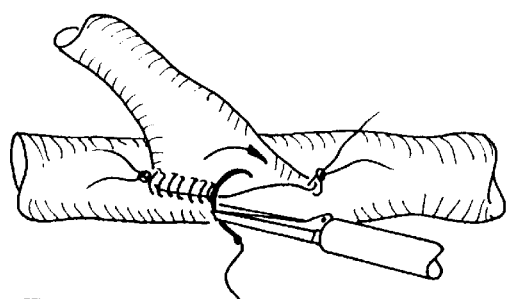
Figure 10H:
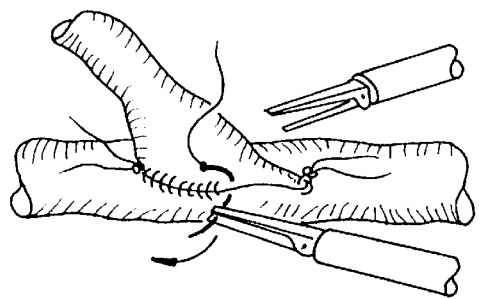
Figure 10I:
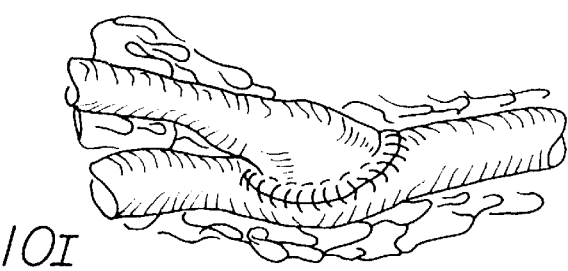
Figure 22:
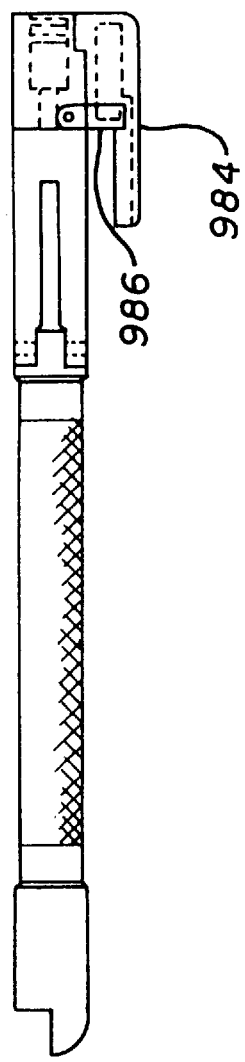
FIG. 22 is an alternative embodiment of a handle in accordance with the present invention.
Figure 21:
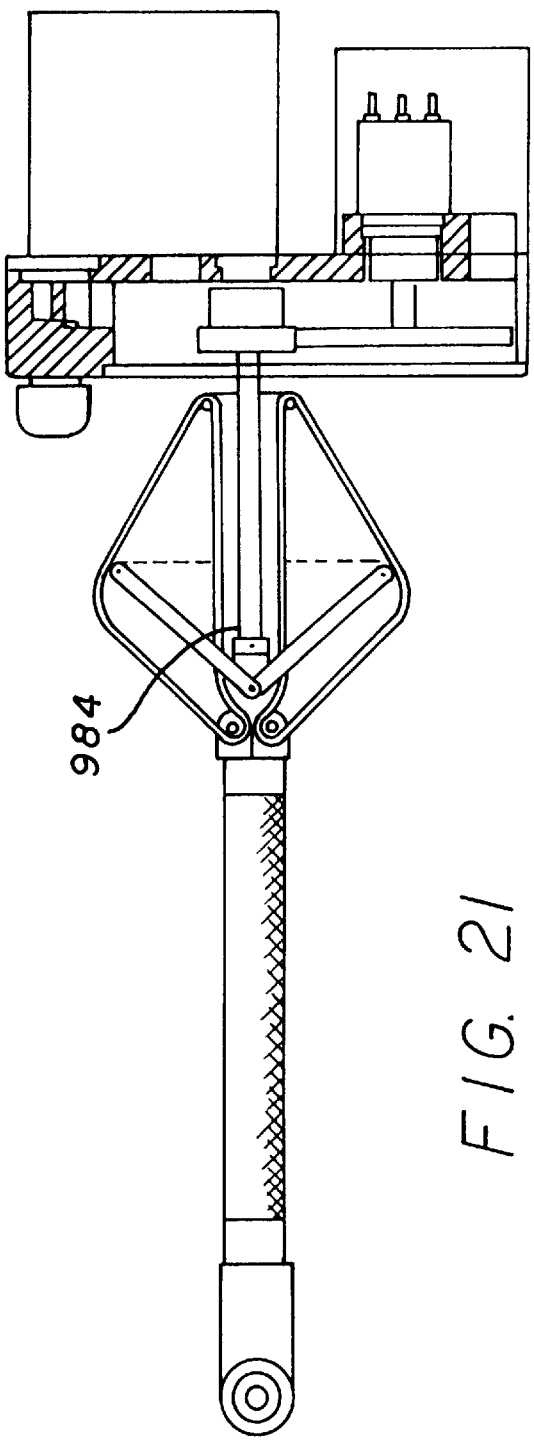
FIG. 21 is a top plan cross-sectional view of the handle depicted in FIG. 20.

Referring to FIGS. 10A–I, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D–F, a new needle and thread can be inserted into the chest cavity to suture the toe of the graft artery to the coronary artery. As shown in FIGS. 10H–I, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

As disclosed hereinabove, the handles 50 and 52 allow a surgeon to control the movement of the tools attached to the robotic arms. As such, the configuration of the handles 50 and 52 should provide great ease of use for a surgeon. FIGS. 34–39 depict various handle configurations. Additionally, the handles 50 and 52 may be selected by a surgeon from a plurality of handles 960 that are available for use by the surgeon.

A proximally open handle 962 has a proximal end 963 and a distal end 965. The handle 962 has first finger portion 964 and a second finger portion 966 pivotally attached at the distal end 965 of the handle 962. A joint 968 disposed intermediate the finger portion 964 and 966 provides linear motion of an elongated rod 970 which is used to actuate the tool tip of an instrument attached to the robotic arm. This handle may serve as one or both of the two handles 50 and 52 of the system.

A distally open handle 972 has a proximal end 973 and a distal end 975. The handle 972 has first finger portion 974 and a second finger portion 976 pivotally attached at the proximal end 973 of the handle 972. A joint 978 disposed intermediate the finger portion 964 and 966 provides linear motion of an elongated rod 980 which is used to actuate the tool tip of an instrument attached to the robotic arm. This handle may serve as one or both of the two handles 50 and 52 of the system.

Either of the handles 962 or 972 may include a locking mechanism. The locking mechanism 963 allows the surgeon to move the first and second finger portions together until they are locked and remain statically positioned relative to each other. Such a locking mechanism may be a toggle lock such that pressing the first and second finger portions towards one another releases the locking mechanism once it has been engaged. The locking mechanism 963 allows the surgeon to grasp a needle, or other object or tissue and then lock the handles so that a constant pressure does not have to be supplied by the surgeon's hand. This helps to ease in use of the system. The locking mechanism may be a toggle lock as that described. Alternatively the locking mechanism may be implemented via a push button or other well known means for actuation. It is preferable that the mechanism be included as part of the handle as this is intuitively used by the surgeon.

Such handles 962 and 972 may be interchanged through the inclusion of an interchange mechanism 984. The interchange mechanism 984 includes a biased detent latch 986 that engages an aperture in the elongated rod 932 such that the handle may be attached or removed from the rod 932.

Other handle configurations are depicted in FIGS. 37–39. And more particularly, each of the handles 1000, 1100, and 1200 have a pair of fingerseats 1020. The major difference between each of the handles 1000, 1100, and 1200 is the orientation of the fingerseats to a pivot point on the handle. The fingerseats may be parallel, or perpendicular to the axis S of the pivot point of the handle. Each of these configurations may be included as an attachable handle. As such, a surgeon may exchange handles throughout a procedure depending upon the task to be accomplished. A surgeon may prefer one handle for a set of tasks and another handle for a different set of tasks. As such, the surgeon may exchange handles during the performance of a surgical procedure to enable such tasks.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotic system for performing minimally invasive surgical procedures, the system generally comprising:
   a surgeon input device;
   a controller connected to the surgeon input device, the controller having at least one output port for providing signals indicative of movement at the surgeon input device;
   at least one robotic arm connected to the output port of the controller; and
   wherein movement of the surgeon input device results in a proportional filtered movement at the at least one cooperating robotic arm.

2. The system of claim 1 further comprising an endoscopic surgical instrument removably attached to the at least one robotic arm.

3. The system of claim 2 wherein said endoscopic surgical instrument comprises a hollow tube.

4. The system of claim 3 wherein the endoscopic surgical instrument comprises a suction tube disposed interior the hollow tube.

5. The system of claim 3 wherein the endoscopic surgical instrument comprises an irrigation tube disposed interior the hollow tube.

6. The system of claim 1 further comprising a robotically positioned endoscope, said robotically positioned endoscope electrically connected to a first video monitor.

7. The system of claim 1 further comprising a second robotically positioned endoscope, said second endoscope electrically connected to a second video monitor.

8. The system of claim 1 wherein the surgeon input device comprises a plurality of removably attachable handles, wherein a surgeon may interchange said handles.

9. The system of claim 8 wherein said plurality of handles comprises a locking mechanism.

10. The system of claim 9 wherein said locking mechanism is a toggle locking mechanism.

11. A robotic system for performing minimally invasive surgical procedures, the system generally comprising:
    a surgeon input device;
    a controller connected to the surgeon input device, the controller having at least one output port for providing signals indicative of movement at the surgeon input device;
    at least one robotic arm connected to the output port of the controller;
    an endoscopic instrument removably attached to the at least one robotic arm; and
    wherein movement at the surgeon input device results in a proportional filtered movement at the at least one cooperating robotic arm.

12. The system of claim 11 wherein the endoscopic surgical instrument further comprises a force reflective element.

13. The system of claim 12 wherein said endoscopic surgical instrument comprises a hollow tube.

14. The system of claim 13 wherein the endoscopic surgical instrument comprises a suction tube disposed interior the hollow tube.

15. The system of claim 3 wherein the endoscopic surgical instrument comprises an irrigation tube disposed interior the hollow tube.

16. The system of claim 11 further comprising a robotically positioned endoscope, said robotically positioned endoscope electrically connected to a first video monitor.

* * * * *